(12) United States Patent
Osugi et al.

(10) Patent No.: US 7,592,372 B2
(45) Date of Patent: Sep. 22, 2009

(54) LIQUID DRUG PREPARATIONS

(75) Inventors: Tomohiko Osugi, Chiba (JP); Masunari Fushimi, Chiba (JP); Yutaka Murata, Chiba (JP); Tetsuo Kaneko, Chiba (JP); Katsumi Imamori, Chiba (JP)

(73) Assignee: Hisamitsu Pharmaceutical Co., Inc., Tosu-shi (JP)

( * ) Notice: Subject to any disclaimer, the term of this patent is extended or adjusted under 35 U.S.C. 154(b) by 674 days.

(21) Appl. No.: 10/477,758

(22) PCT Filed: May 24, 2002

(86) PCT No.: PCT/JP02/05043

§ 371 (c)(1),
(2), (4) Date: Nov. 25, 2003

(87) PCT Pub. No.: WO02/096407

PCT Pub. Date: Dec. 5, 2002

(65) Prior Publication Data

US 2004/0147609 A1 Jul. 29, 2004

(30) Foreign Application Priority Data

May 25, 2001 (JP) .............................. 2001-156840

(51) Int. Cl.
*A61K 31/195* (2006.01)
*A61K 31/198* (2006.01)
*A61K 9/08* (2006.01)

(52) U.S. Cl. ........................................ 514/562; 424/49

(58) Field of Classification Search .................. 514/561, 514/562; 424/464, 49
See application file for complete search history.

(56) References Cited

U.S. PATENT DOCUMENTS 5,047,428 A     9/1991    Itoh et al.

FOREIGN PATENT DOCUMENTS

| EP | 998926 | 5/2000 |
|---|---|---|
| JP | 63-156719 | 6/1988 |
| JP | A 63-156719 | * 12/1988 |
| JP | 2-3674 | 1/1990 |
| JP | 5-58887 | 3/1993 |
| JP | 5-58888 | 3/1993 |
| JP | 11-35459 | 2/1999 |
| JP | 2000-256192 | 9/2000 |

OTHER PUBLICATIONS

Koichi Takahashi et al, Effects of SS320A, a New Cysteine Derivative, on the Change in the Number of Goblet Cells Induced by Isoproterenol in Rat Tracheal Epithelium, Jpn. J. Pharmacol. 77, 71-77 (1998).*
Barnsley; The Formation of 2-Hydroxypropylmercapturic Acid from 1-Halogenopropanes in the Rat; 1996; Biochem. J.; vol. 100; p. 362-372.*

* cited by examiner

*Primary Examiner*—Ardin Marschel
*Assistant Examiner*—Zohreh Vakili
(74) *Attorney, Agent, or Firm*—Oblon, Spivak, McClelland, Maier & Neustadt, L.L.P.

(57) ABSTRACT

Liquid drug preparations characterized by containing fudostein and an acid together with a sweetener such as sugar alcohol, trehalose or a sweetener having a high degree of sweetness. These liquid drug preparations are fudostein-containing liquid drug preparations which are free from color change or sedimentation upon prolonged storage and can be easily taken.

9 Claims, No Drawings

LIQUID DRUG PREPARATIONS

CROSS REFERENCE TO RELATED APPLICATIONS

The present application is a 371 application of PCT/JP02/05043 filed May 24, 2002.

TECHNICAL FIELD

The present invention relates to a liquid drug preparation containing fudostein and, more particularly, to a liquid drug preparation that is free from color change and sedimentation during storage for a long period of time notwithstanding inclusion of fudostein and can be advantageously used as an expectorant.

BACKGROUND ART

Fudostein is a nonproprietary name for S-(3-hydroxypropyl)-L-cysteine of the following formula (I) and is useful as a drug exhibiting an expectorative effect (Examined Japanese Patent Publication No. 7-88352).

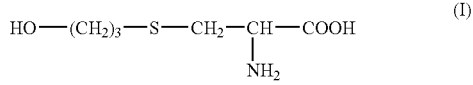

(I)

Patients of chronic bronchitis or bronchial asthma have fat respiratory epithelium submucosal glands, secrete an increased amount of epithelium mucus due to excessive formation of goblet cells, and suffer from expectoration difficulties due to excessive secretion of mucin during sickness. For these reasons, these patients have subjective symptoms such as phlegm blocking the peripheral respiratory tract in the breast and difficulty in ejecting phlegm in the central respiratory tract. Fudostein is highly useful as an expectorant, since the drug can significantly improve these symptoms at a clinical dose.

Conventionally, a solid preparation using a starch, for example, as a carrier has been known as a fudostein preparation (Japanese Patent Application Laid-open No.11-35459). However, there has been no liquid fudostein preparation that can be easily taken by a patient of asthma and the like due to a problem of stability.

The reason is because a fudostein solution exhibits change in color and produces sedimentation over time. Although these phenomena have no direct effect on the drug efficacy, the change in color and sedimentation cause anxiety among the patients orally taking the drug and remarkably decrease the commercial value of the drug. Since fudostein has a peculiar taste that gives an unfavorable sensation upon dosing, the fudostein is preferably made into a syrup preparation by adding a sweetener. However, sucrose and glucose commonly used for syrup preparations, if added to a fudostein syrup preparation, react with fudostein and darken the color of the solution. This phenomenon also unduly impairs the commercial value.

Therefore, development of a fudostein-containing liquid drug preparation free from color change and sedimentation during long-term storage can be easily taken has been desired. An object of the present invention is to provide such a liquid drug preparation.

DISCLOSURE OF THE INVENTION

As a result of extensive studies on compositions of fudostein liquid preparations and additives to such compositions to achieve the above object, the inventors of the present invention have found that fudostein is easily discolored in a neutral region, but changes color only with difficulty and does not have a problem of sedimentation in an acidic region. The inventors have further found that if sugar alcohol, trehalose, or a sweetener having a high degree of sweetness is used as the sweetener, the problem of browning of the solution can be avoided. These findings have led to completion of the present invention.

Specifically, the present invention provides a liquid drug preparation comprising fudostein and an acid.

The present invention also provides a liquid drug preparation comprising sugar alcohol, trehalose, or a sweetener having a high degree of sweetness as the sweetener.

BEST MODE FOR CARRYING OUT THE INVENTION

The liquid drug preparation of the present invention can be prepared by adding an acid to a solution of fudostein to provide a solution having an acidic pH according to a conventional method.

Although there are no specific limitations, the content of fudostein contained as the effective component in the liquid drug preparation of the present invention is about 1-20 wt/vol % (hereinafter indicated as "%"), preferably 2-10%, and still more preferably 4-8%.

Water is used as the solvent for dissolving fudostein. Optionally, other solvents such as dehydrated ethanol, ethanol, propylene glycol, concentrated glycerin, glycerol, glyceride, polyoxyethylene hydrogenated castor oil 60, polyoxyl 35 castor oil, polysorbate 20, polysorbate 40, polysorbate 60, polysorbate 80, Macrogol 200, Macrogol 300, Macrogol 400, Macrogol 600, Macrogol 4000, and Lauromacrogol can be added.

As the acid added to the liquid drug preparation of the present invention, organic acids and inorganic acids can be given. As an inorganic acid, hydrochloric acid, phosphoric acid, sulfuric acid, and the like can be used. As an organic acid, acetic acid, malic acid, citric acid, tartaric acid, lactic acid, fumaric acid, succinic acid, adipic acid, gluconic acid, glucono-d-lactone, and the like can be used. These acids may be used either individually or in combination of two or more.

The liquid drug preparation of the present invention may have an acidic pH, if the above acid is added. The pH is preferably 5.0 or less, and more preferably 4.0-2.5.

Preferably, a sweetener such as sugar alcohol, trehalose, or a sweetener having a high degree of sweetness can be further added to the liquid drug preparation of the present invention. As examples of the sugar alcohol that can be added, polyhydric alcohols with a chain structure obtained by reducing the carbonyl group of aldose or ketose and cyclic sugar alcohols can be given. Specific examples include polyhydric alcohols with a chain structure having 3-11 carbon atoms such as D-sorbitol, D-mannitol, xylitol, erythritol, D-arabitol, and dulcitol, and cyclic sugar alcohols such as maltitol, platinit (reduced palatinose), xylose, inositol, and lactitol. Of these, D-sorbitol, D-mannitol, xylitol, and erythritol are preferable. As examples of the high sweetness sweetener, stevia, aspartame, thaumatin, sucralose, saccarin and its salt, and glycyrrhizic acid and its salt can be given. Of these, stevia, aspartame, saccarin, and sodium saccharin are preferable. These sweeteners may be used either individually or in combination of two or more.

When the sugar alcohol or trehalose is used in the liquid drug preparation of the present invention, the amount incorporated is 1-50%, preferably 5-40%, and more preferably 10-30%. If the sweetener with a high degree of sweetness is added, the amount added is 0.01-1.0%. The addition of the sweetener in an amount of this range masks the peculiar taste possessed by fudostein, while preventing browning of the solution.

Any optional components that are pharmaceutically acceptable can be further added to the liquid drug preparation of the present invention. Such optional components include thickeners such as sodium alginate, carboxyvinyl polymer, carmellose sodium, xanthan gum, crystalline cellulose.carmellose sodium, hydroxyethyl cellulose, hydroxypropylcellulose, hydroxypropyl methylcellulose, and polyvinyl alcohol; preservatives such as sorbic acid or its salt, benzoic acid or its salt, parabenes (ethyl parahydroxybenzoate, methyl p-oxybenzoate, butyl p-oxybenzoate, propyl parahydroxybenzoate, etc.); colorants such as natural colorants (caramel, β-carotene, etc.) and artificial colorants (edible dyes, sodium riboflavin phosphate, etc.); and perfumes such as orange oil, lemon oil, menthol, vanillin, fruit flavors (strawberry, pineapple, orange, apple, lemon, lime, grapefruit, etc.), crude drug flavors (herb, mint, etc.), beverage-type flavors (cocoa, tea, lemon soda, etc.), and confectionery-type flavors (chocolate, yoghurt, etc.).

The liquid drug preparation of the present invention made in the above manner can be used as an oral expectorant and the like.

EXAMPLES

The present invention will be described in more detail by way of examples which should not be construed as limiting the present invention.

Example 1

Study of the influence of pH on fudostein liquid preparations:

Aqueous solutions containing 8 g of fudostein were adjusted to pH 2-7 using an appropriate amount of phosphoric acid or sodium hydroxide as shown in Table 1. Purified water was added to make the total amount of each solution 100 ml, thereby obtaining liquid fudostein preparations with different pHs. The liquid preparations were preserved at 70° C. for seven days to examine the residual ratio of fudostein in the solutions, color change, and sedimentation. The residual ratio of fudostein was calculated from the amount of fudostein determined by quantitative analysis using HPLC. The color change and sedimentation were evaluated by naked eye observation and rated according to the following standard. The results are shown in Table 1.

Evaluation standard for color change:

Rate: Evaluation results
(−): There was no color change in the liquid preparation.
(±): There was slight color change in the liquid preparation.
(+): There was color change in the liquid preparation.
(++): There was remarkable color change in the liquid preparation.

Evaluation standard for sedimentation
Rate: Evaluation results
(−): No sedimentation was observed.
(±): Slight sedimentation was observed.
(+): Sedimentation was observed.

(Results)

TABLE 1

|  | pH 7.0 | pH 6.0 | pH 5.0 | pH 4.0 | pH 3.5 | pH 3.0 | pH 2.5 | pH 2.0 |
| --- | --- | --- | --- | --- | --- | --- | --- | --- |
| Analytical value Residual ratio (%) | 99.4 | 100.4 | 100.1 | 101.1 | 100.3 | 100.7 | 100.0 | 99.9 |
| Color change | ++ | + | ± | − | − | − | − | − |
| Sedimentation | − | − | − | − | − | − | ± | ± |

As a result, the liquid fudostein preparation was confirmed to remain stable at pH 5.0 or less, particularly at a pH in the range of 3.0-4.0. In addition, there was almost no change in the pH of each solution, i.e. the pH change after seven days was within an allowable error range.

Example 2

Study of the type of pH adjuster for fudostein liquid preparation:

Aqueous solutions containing 8 g of fudostein were adjusted to pH 3.5 by adding various acids shown in Table 2. Purified water was added to make the total amount of each solution 100 ml, thereby obtaining liquid fudostein preparations. The liquid preparations were preserved at 70° C. for seven days to evaluate color change in the same manner as in Example 1. The results are shown in Table 2.

(Results)

TABLE 2

|  | Analytical value Residual ratio (%) | Color change |
| --- | --- | --- |
| Hydrochloric acid | 99.7 | − |
| Phosphoric acid | 100.5 | − |
| Sulfuric acid | 100.3 | − |
| Acetic acid | 101.2 | − |
| Malic acid | 99.3 | − |
| Citric acid | 100.7 | − |
| Tartaric acid | 100.7 | − |
| Lactic acid | 99.5 | − |
| Fumaric acid | 98.8 | − |

As a result, both inorganic acids and organic acids were confirmed to be usable in the liquid drug preparation of the present invention. In addition, there was almost no change in the pH of each solution due to the addition of acids, i.e. the pH change after seven days was within an allowable error range.

Example 3

Study of the type of sweetener for fudostein liquid preparation:

Aqueous solutions containing 8 g of fudostein and 20 g of sweeteners shown in Table 3 were adjusted to pH 3.5 by adding phosphoric acid. Purified water was added to make the total amount of each solution 100 ml, thereby obtaining liquid fudostein preparations. The liquid preparations were preserved at 70° C. for seven days to evaluate color change in the same manner as in Example 1. The results are shown in Table 3.

(Results)

TABLE 3

|  | Analytical value Residual ratio (%) | Color change |
| --- | --- | --- |
| Purified white sugar | 90.5 | ++ |
| Glucose | 78.8 | ++ |
| Fructose | 90.7 | ++ |
| Isomerized sugar | 90.8 | ++ |
| D-sorbitol | 100.7 | – |
| D-mannitol | 99.3 | – |
| Xylytol | 100.3 | – |
| Erythritol | 99.5 | – |
| Trehalose | 100.2 | – |
| Reduced malt sugar syrup* | 99.9 | – |

*A mixture of maltitol, sorbitol, and oligosaccharide alcohol

As a result, the use of sugar alcohol or trehalose as a sweetener was confirmed to maintain a high residual ratio of fudostein and prevent color change. In addition, there was almost no change in the pH of each solution due to the addition of the sweeteners, i.e. the pH change after seven days was within an allowable error range.

Example 4

Study of the type of sweetener for fudostein liquid preparation:

Aqueous solutions containing 8 g of fudostein and 0.1-0.2 g of sweeteners shown in Table 4 were adjusted to pH 3.5 by adding phosphoric acid. Purified water was added to make the total amount of each solution 100 ml, thereby obtaining liquid fudostein preparations. The liquid preparations were preserved at 70° C. for seven days to evaluate color change in the same manner as in Example 1. The results are shown in Table 4.

(Results)

TABLE 4

|  | Amount (g) | Analytical value Residual ratio (%) | Color change |
| --- | --- | --- | --- |
| Stevia | 0.2 | 100.4 | – |
| Aspartame, | 0.2 | 99.1 | – |
| Sodium saccharin | 0.1 | 99.4 | – |

As a result, the use of sweeteners with a high degree of sweetness was confirmed to maintain a high residual ratio of fudostein and prevent color change.

Example 5

Study of the amount of sugar alcohol in fudostein liquid preparation:

Aqueous solutions containing 8 g of fudostein and D-sorbitol in the amounts shown in Table 5 were adjusted to pH 3.5 by adding phosphoric acid. Purified water was added to make the total amount of each solution 100 ml, thereby obtaining liquid fudostein preparations. The liquid preparations were preserved at 70° C. for seven days to evaluate the residual ratio, color change, and sedimentation in the same manner as in Example 1. The results are shown in Table 5.

(Results)

TABLE 5

|  | Analytical value Residual ratio (%) | Color change | Sedimentation |
| --- | --- | --- | --- |
| 0% | 99.6 | – | – |
| 10% | 99.4 | – | – |
| 20% | 99.0 | – | – |
| 30% | 99.3 | – | – |
| 40% | 99.9 | ± | + |
| 50% | 100.4 | + | + |

As a result, liquid fudostein preparations with a sugar alcohol concentration of 40% or less, particularly 30% or less, were confirmed to be stable stable. In addition, there was almost no change in the pH of each solution due to the D-sorbitol content, i.e. the pH change after seven days was within an allowable error range.

Example 6

Fudostein-containing oral liquid drug preparation:

An oral liquid drug preparation with the following formulation was prepared according to a conventional manner. The pH of the liquid drug preparation was 3.7.

| Component) | Amount (wt %) |
| --- | --- |
| Fudostein | 8 g |
| D-sorbitol | 15 g |
| Caramel | 100 mg |
| Sodium benzoate | 70 mg |
| Malic acid | Appropriate amount |
| Perfume (yoghurt-type) | 100 mg |
| Purified water | Balance |
| Total amount | 100 ml |

The preparation was stable with no decrease in the fudostein content, no color change, and no sedimentation. The peculiar taste of fudostein was masked by the addition of D-sorbitol and perfume.

Example 7

Fudostein-containing oral liquid drug preparation:

An oral liquid drug preparation with the following formulation was prepared according to a conventional manner.

The pH of the liquid drug preparation was 3.7.

| Component | Amount (wt %) |
| --- | --- |
| Fudostein | 8 g |
| Erythritol | 20 g |
| Caramel | 100 mg |
| Sodium benzoate | 70 mg |
| Phosphoric acid | Appropriate amount |
| Perfume (orange-type) | 100 mg |
| Purified water | Balance |
| Total amount | 100 ml |

The preparation was stable with no decrease in the fudostein content, no color change, and no sedimentation. The peculiar taste of fudostein was masked by the addition of erythritol and perfume.

Example 8

Fudostein-containing oral liquid drug preparation:

An oral liquid drug preparation with the following formulation was prepared according to a conventional manner. The pH of the liquid drug preparation was 3.7.

| Component | Amount (wt %) |
| --- | --- |
| Fudostein | 8 g |
| Reduced malt sugar syrup* | 20 g |
| Caramel | 100 mg |
| Sodium benzoate | 70 mg |
| Malic acid | Appropriate amount |
| Perfume (menthol-type) | 100 mg |
| Purified water | Balance |
| Total amount | 100 ml |

*A mixture of maltitol, sorbitol, and oligosaccharide alcohol

The preparation was stable with no decrease in the fudostein content, no color change, and no sedimentation. The peculiar taste of fudostein was masked by the addition of reduced malt sugar syrup and perfume.

Example 9

Fudostein-containing oral liquid drug preparation:

An oral liquid drug preparation with the following formulation was prepared according to a conventional manner. The pH of the liquid drug preparation was 3.7.

| Component | Amount (wt %) |
| --- | --- |
| Fudostein | 8 g |
| Trehalose | 20 g |
| Caramel | 100 mg |
| Sodium benzoate | 70 mg |
| Phosphoric acid | Appropriate amount |
| Perfume (chocolate-type) | 100 mg |
| Purified water | Balance |
| Total amount | 100 ml |

The preparation was stable with no decrease in the fudostein content, no color change, and no sedimentation. The peculiar taste of fudostein was masked by the addition of trehalose and perfume.

Example 10

Fudostein-containing oral liquid drug preparation:

An oral liquid drug preparation with the following formulation was prepared according to a conventional manner. The pH of the liquid drug preparation was 3.7.

| Component | Amount (wt %) |
| --- | --- |
| Fudostein | 8 g |
| Stevia | 100 mg |
| Caramel | 100 mg |
| Sodium benzoate | 70 mg |
| Malic acid | Appropriate amount |
| Perfume (strawberry-type) | 100 mg |
| Purified water | Balance |
| Total amount | 100 ml |

The preparation was stable with no decrease in the fudostein content, no color change, and no sedimentation. The peculiar taste of fudostein was masked by the addition of stevia and perfume.

INDUSTRIAL APPLICABILITY

The liquid drug preparation of the present invention is highly stable and free from color change and sedimentation during a long storage period in spite of the inclusion of fudostein. In addition, the liquid drug preparation comprising sugar alcohol, trehalose, or a sweetener having a high degree of sweetness as a sweetener masks the peculiar taste of fudostein without causing a problem of browning of the solution. The liquid drug preparation of the present invention is therefore has a high commercial value as a expectorant and the like as an oral liquid preparation that can be easily taken.

The invention claimed is:

1. A liquid drug preparation comprising fudosteine and an acid and having a pH of 2.5 to 4.0, wherein the liquid drug preparation is formulated to be suitable for oral administration in a patient in need of fudosteine administration.

2. The liquid drug preparation according to claim 1, further comprising sugar alcohol in an amount of less than 40% by mass, trehalose in an amount of less than 40% by mass, or a sweetener having a high degree of sweetness as a sweetener in an amount of 0.01 to 1.0% by mass.

3. The liquid drug preparation according to claim 2, comprising the sugar alcohol which is D-sorbitol, D-mannitol, xylytol, or erythritol.

4. The liquid drug preparation according to claim 2, comprising the sweetener having a high degree of sweetness which is stevia, aspartame, saccharin, or sodium saccharin.

5. The liquid drug preparation according to claim 1, wherein the acid is selected from the group consisting of hydrochloric acid, phosphoric acid, sulfuric acid, malic acid, citric acid, tartaric acid, lactic acid, fumaric acid, and combinations thereof.

6. The liquid drug preparation according to claim 2, wherein the acid is selected from the group consisting of hydrochloric acid, phosphoric acid, sulfuric acid, malic acid, citric acid, tartaric acid, lactic acid, fumaric acid, and combinations thereof.

7. The liquid drug preparation according to claim 3, wherein the acid is selected from the group consisting of hydrochloric acid, phosphoric acid, sulfuric acid, malic acid, citric acid, tartaric acid, lactic acid, fumaric acid, and combinations thereof.

8. The liquid drug preparation according to claim 4, wherein the acid is selected from the group consisting of hydrochloric acid, phosphoric acid, sulfuric acid, malic acid, citric acid, tartaric acid, lactic acid, fumaric acid, and combinations thereof.

9. A liquid drug preparation comprising fudosteine and an acid and having a ph of 3.0 to 4.0.

* * * * *